(12) United States Patent
Boogaard et al.

(10) Patent No.: US 7,769,471 B1
(45) Date of Patent: *Aug. 3, 2010

(54) IMPLANTABLE CABLE HAVING SECURELY ATTACHED RING CONTACTS AND METHODS OF MANUFACTURING THE SAME

(75) Inventors: Jerome J. Boogaard, Forest Grove, OR (US); Robert W. Lucas, Prineville, OR (US); John W. Swanson, Portland, OR (US); Sergey N. Varivoda, Vancouver, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 494 days.

This patent is subject to a terminal disclaimer.

(21) Appl. No.: 11/767,263

(22) Filed: Jun. 22, 2007

Related U.S. Application Data

(63) Continuation of application No. 10/700,110, filed on Nov. 3, 2003, now Pat. No. 7,239,922.

(51) Int. Cl.
*A61N 1/36* (2006.01)
(52) U.S. Cl. ...................................... 607/116
(58) Field of Classification Search ............... 607/116
See application file for complete search history.

(56) References Cited

U.S. PATENT DOCUMENTS

| | | | |
|---|---|---|---|
| 4,590,950 A * | 5/1986 | Iwaszkiewicz et al. | 607/119 |
| 4,944,088 A * | 7/1990 | Doan et al. | 29/858 |
| 5,251,643 A * | 10/1993 | Osypka | 607/122 |
| 5,514,172 A * | 5/1996 | Mueller | 607/122 |
| 6,181,971 B1 * | 1/2001 | Doan | 607/116 |
| 6,505,401 B1 * | 1/2003 | Doan | 29/860 |

* cited by examiner

*Primary Examiner*—Carl H Layno
*Assistant Examiner*—Eric D. Bertram
(74) *Attorney, Agent, or Firm*—Christopher S. L. Crawford; Peter Lando; Melissa Acosta

(57) ABSTRACT

In one embodiment, a method of manufacturing a biological electrical stimulus cable assembly, comprises: providing a cable portion including a plurality of first conductive wires; removing a first portion of the insulative material from a surface along the length of the insulative material at a first location to expose only one of the first conductive wires; electrically connecting a second conductive wire to the first exposed wire surface; wrapping the second conductive wire about the cable portion a plurality of times around the cable portion such that the second conductive wire forms a substantially continuous band; electrically connecting a second end of the second conductive wire to a conductive surface; and providing an electrode over the band formed by the second conductive wire, wherein the band formed by the second conductive wire extends along at least a majority of the length of the electrode.

10 Claims, 2 Drawing Sheets

IMPLANTABLE CABLE HAVING SECURELY ATTACHED RING CONTACTS AND METHODS OF MANUFACTURING THE SAME

RELATED APPLICATION

The present application is a continuation of U.S. patent application Ser. No. 10/700,110, entitled "IMPLANTABLE CABLE HAVING SECURELY ATTACHED RING CONTACTS AND METHODS OF MANUFACTURING THE SAME," filed Nov. 3, 2003, now U.S. Pat. No. 7,239,922, which is incorporated herein by reference.

BACKGROUND

Cables that are designed to be implanted in a patient, typically for pain management or other neurological stimulation, are generally fitted with a series of ring contacts. A ring contact, which circumscribes the cable, makes contact with the desired location inside the patient's body, regardless of the orientation of the cable.

The presently used technique for attaching the ring connectors is somewhat cumbersome. Typically, each individual wire is stripped and a ring fixture is crimped onto it. This operation requires a fair amount of manual labor, requiring fine coordination, and is, therefore, quite expensive.

SUMMARY

In one embodiment, a method of manufacturing a biological electrical stimulus cable assembly, comprises: providing a cable portion including a plurality of first conductive wires, wherein the plurality of first conductive wires are enclosed within the insulative material that forms a body of the cable portion; removing a first portion of the insulative material from a surface along the length of the insulative material at a first location to expose only one of the first conductive wires thereby creating a first exposed wire surface, wherein the removing the first portion is performed on the cable portion after the plurality of first conductive wires are disposed within the insulative material of the body of the cable portion; electrically connecting a first end of a second conductive wire to the first exposed wire surface; wrapping the second conductive wire about the cable portion, wherein the wrapping causes the second conductive wire to be wrapped a plurality of times around the cable portion such that the second conductive wire forms a substantially continuous band around the cable portion; electrically connecting a second end of the second conductive wire to a conductive surface; and providing an electrode over the band formed by the second conductive wire, wherein the band formed by the second conductive wire extends along at least a majority of the length of the electrode.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
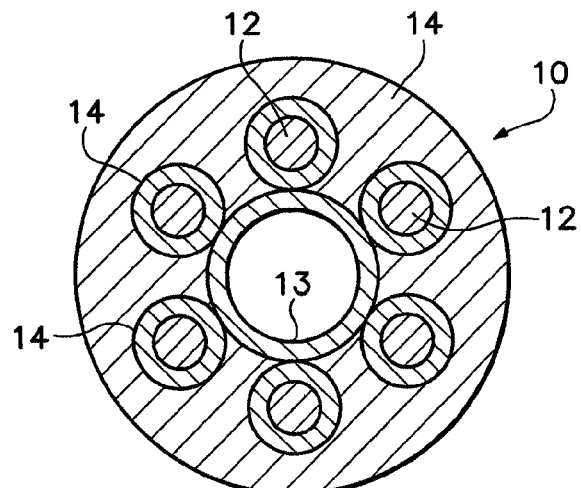
FIG. 1 is a cross-sectional view of a set of wires held within insulative material, according to a first step in a method of one representative embodiment.
Figure 2:
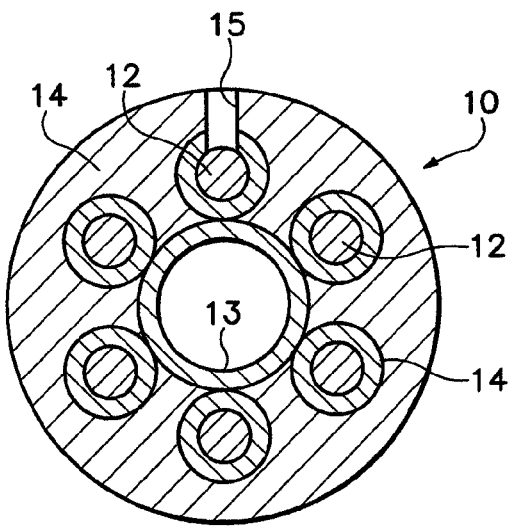
FIG. 2 is a cross-sectional view of the structure of FIG. 1, after a further step in a method of one representative embodiment.
Figure 3:
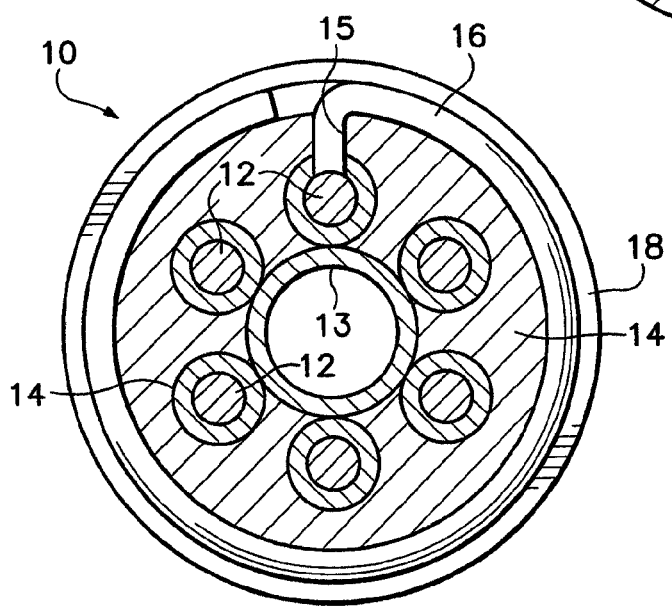
FIG. 3 is a cross-sectional view of the structure of FIG. 1 after another step in a method of one representative embodiment.

Referring to FIGS. 1-3, a preferred method of practicing the invention begins with a cable portion 10 having a set of first conductive wires 12 set into a double layered structure of insulative material 14 about a tube 13. In an alternative preferred embodiment, a wire is placed in the center of cable portion 10 to impart longitudinal strength to cable portion 10.

Figure 4:
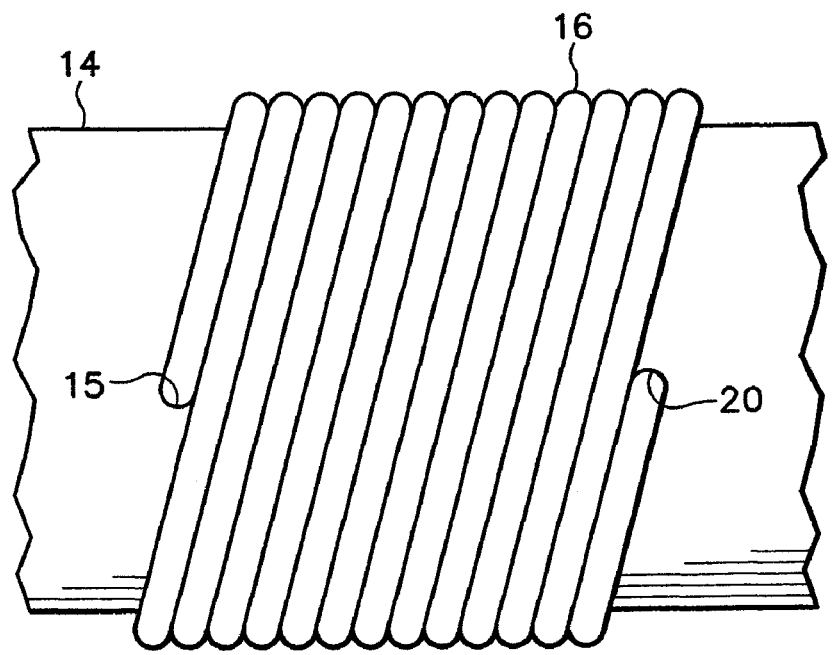
FIG. 4 is a perspective view of the structure of FIG. 1, showing a wire connected in two places according to one representative embodiment.
Figure 5:
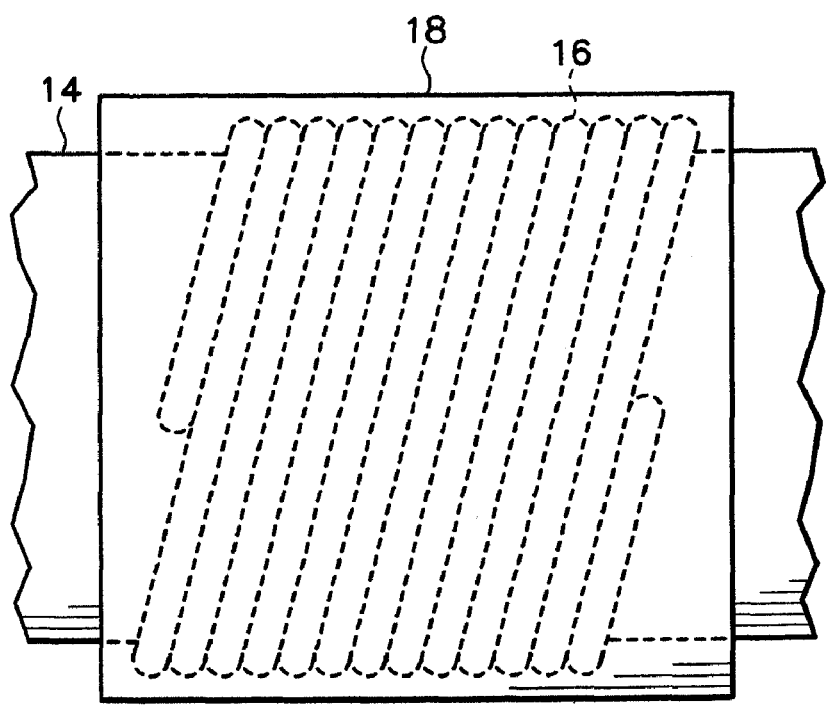
FIG. 5 is a perspective view of a finished product constructed according to the steps of FIGS. 1, 2, and 3.

A laser is used to ablate an aperture 15 (FIG. 2) through insulative material 14 and a second conductive wire 16 is threaded through this aperture 15 into contact with a first conductive wire 12, to which it is laser welded or otherwise attached. A drop of epoxy may then be added into aperture 15, to better secure wire 16. Wire 16 is then wrapped about cable portion 10 and welded to a conductive ring 18 (FIG. 3) that has been placed about cable portion 10. The result is a connection between first conductive wire 12 and conductive ring 18 that is both electrically and structurally robust. In a particular preferred embodiment, shown in FIG. 4, an additional aperture 20 is formed through insulative material 14, spaced apart longitudinally from aperture 15. Wire 16 is then attached to wire 12 by way of aperture 15, wound about cable portion 10 and then attached again to wire 12 through aperture 20. This provides a particularly robust attachment for wire 16 and provides a good amount of surface area to form an excellent electrical connection with ring 18, which is threaded directly radially over wire 16. In an alternative preferred embodiment, wire 16 is wrapped about cable portion 10 a single time only, as it stretches from aperture 15 to aperture 20. In another alternative embodiment, wire 16 forms a circumscribing electrode on its own, without the presence of a ring 18 (i.e., FIG. 4 shows the final product).

In an alternative preferred embodiment, a conductive ring 18 is constructed of conductive material directly on the cable portion 10. In an additional alternative preferred embodiment, a partial ring (for example, one that extends through three-quarters of a circle) is used. In one preferred embodiment, cable portion 10 has a diameter of 500 microns, wires 12 are 100 microns thick, wire 16 is 75 microns thick and ring 18 is 50 microns thick and 3,000 microns wide.

Although a frequency multiplied ND:YAG laser is the preferred device for removing insulative material 14, the pulse lengths available from this type of laser are typically not lengthy enough to facilitate laser welding. As a result, for the welding portion of the above described task, the preferred tool is a ND:YAG that is not frequency multiplied or a $CO_2$ laser.

To help hold each ring 18 in place, the cable portion 10 may be over molded after rings 18 have been attached. In this operation, the cable portion 10 is encased in a polymer resin, which does not cover the outer surfaces of rings 18. In this manner rings 18 may be affirmatively retained and not permitted to slide longitudinally.

In some embodiments, ring 18 is placed radially over wire 16, while in a different preferred embodiment, wire 16 abuts ring 18 longitudinally.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of manufacturing a biological electrical stimulus cable assembly, comprising:
providing a cable portion including a plurality of first conductive wires, wherein the plurality of first conductive wires are enclosed within the insulative material that forms a body of the cable portion;
removing a first portion of the insulative material from a surface along the length of the insulative material at a first location to expose only one of the first conductive wires thereby creating a first exposed wire surface, wherein the removing the first portion is performed on the cable portion after the plurality of first conductive wires are disposed within the insulative material of the body of the cable portion;
electrically connecting a first end of a second conductive wire to the first exposed wire surface;
wrapping the second conductive wire about the cable portion, wherein the wrapping causes the second conductive wire to be wrapped a plurality of times around the cable portion such that the second conductive wire forms a substantially continuous band around the cable portion;
electrically connecting a second end of the second conductive wire to a conductive surface; and
providing an electrode over the band formed by the second conductive wire, wherein the band formed by the second conductive wire extends along at least a majority of the length of the electrode.

2. The method of claim 1 wherein the plurality of conductive wires are disposed at substantially the same radial depth within the insulative material.

3. The method of claim 1 further comprising:
removing a second portion of the insulative material from the surface of the length of insulative material at a second location to expose only one of the first conductive wires thereby creating a second exposed wire surface, wherein the removing the second portion is performed on the cable portion after the first conductive wires are disposed within the insulative material of the body of the cable portion.

4. The method of claim 3 wherein the electrically connecting a second end of the second conductive wire comprises electrically connecting the second end of the second conductive wire to the second exposed wire surface.

5. The method of claim 4 wherein the first and second exposed wire surfaces expose different portions of a common conductive wire of the plurality of first conductive wires.

6. The method of claim 1 wherein the electrically connecting a first end of a second conductive wire to the first exposed wire surface comprises:
laser welding the first end of the second conductive wire to the first exposed wire surface.

7. The method of claim 1 wherein the removing a first portion of the insulative material comprises laser ablating insulative material at the first location.

8. The method of claim 1 wherein the electrode is electrically connected to the second conductive wire.

9. The method of claim 1 wherein providing the electrode comprising:
crimping the electrode over the band formed by the second conductive wire.

10. The method of claim 1 wherein the plurality of first conductive wires are set within the insulative material of the cable portion before the removing is performed.

* * * * *